(12) United States Patent
Chin

(10) Patent No.: US 6,610,031 B1
(45) Date of Patent: Aug. 26, 2003

(54) VALVE ASSEMBLY

(75) Inventor: Albert K. Chin, Palo Alto, CA (US)

(73) Assignee: Origin Medsystems, Inc., Menlo Park, CA (US)

( * ) Notice: Subject to any disclaimer, the term of this patent is extended or adjusted under 35 U.S.C. 154(b) by 0 days.

(21) Appl. No.: 09/837,649

(22) Filed: Apr. 18, 2001

(51) Int. Cl.[7] .............................................. A61M 25/00
(52) U.S. Cl. ............................................... 604/167.04
(58) Field of Search ........................ 604/37, 167.01, 604/167.02, 167.03, 167.04, 167.06, 244, 247, 264, 537; 251/149.1; 137/849

(56) References Cited

U.S. PATENT DOCUMENTS

| | | | |
|---|---|---|---|
| 2,023,267 A | * 12/1935 | De Saint Rapt et al. | .......................... 128/202.15 |
| 3,872,525 A | * 3/1975 | Lea et al. | .......................... 5/671 |
| 4,673,393 A | 6/1987 | Suzuki et al. | |
| 5,000,745 A | 3/1991 | Guest et al. | |
| 5,009,391 A | 4/1991 | Steigerwald | |
| 5,030,205 A | 7/1991 | Holdaway et al. | |
| 5,041,095 A | 8/1991 | Littrell | |
| 5,053,013 A | 10/1991 | Ensminger et al. | |
| 5,057,084 A | 10/1991 | Ensminger et al. | |
| 5,092,846 A | 3/1992 | Nishijima et al. | |
| 5,104,389 A | * 4/1992 | Deem et al. | ............ 604/167.02 |
| 5,389,081 A | 2/1995 | Castro | |
| 5,409,463 A | * 4/1995 | Thomas et al. | ......... 604/167.04 |
| 5,507,732 A | 4/1996 | McClure et al. | |
| 5,743,884 A | 4/1998 | Hasson et al. | |
| 6,086,570 A | 7/2000 | Aboul-Hosn et al. | |

* cited by examiner

Primary Examiner—Ehud Gartenberg
Assistant Examiner—Patrick Buechner
(74) Attorney, Agent, or Firm—Blakely, Sokoloff, Taylor & Zafman LLP

(57) ABSTRACT

A valve assembly. The valve assembly can include valve members with passageways partially non-overlapping. A compression member can be, provided adjacent the valve members. The valve assembly can be incorporated into a medical access device.

25 Claims, 4 Drawing Sheets

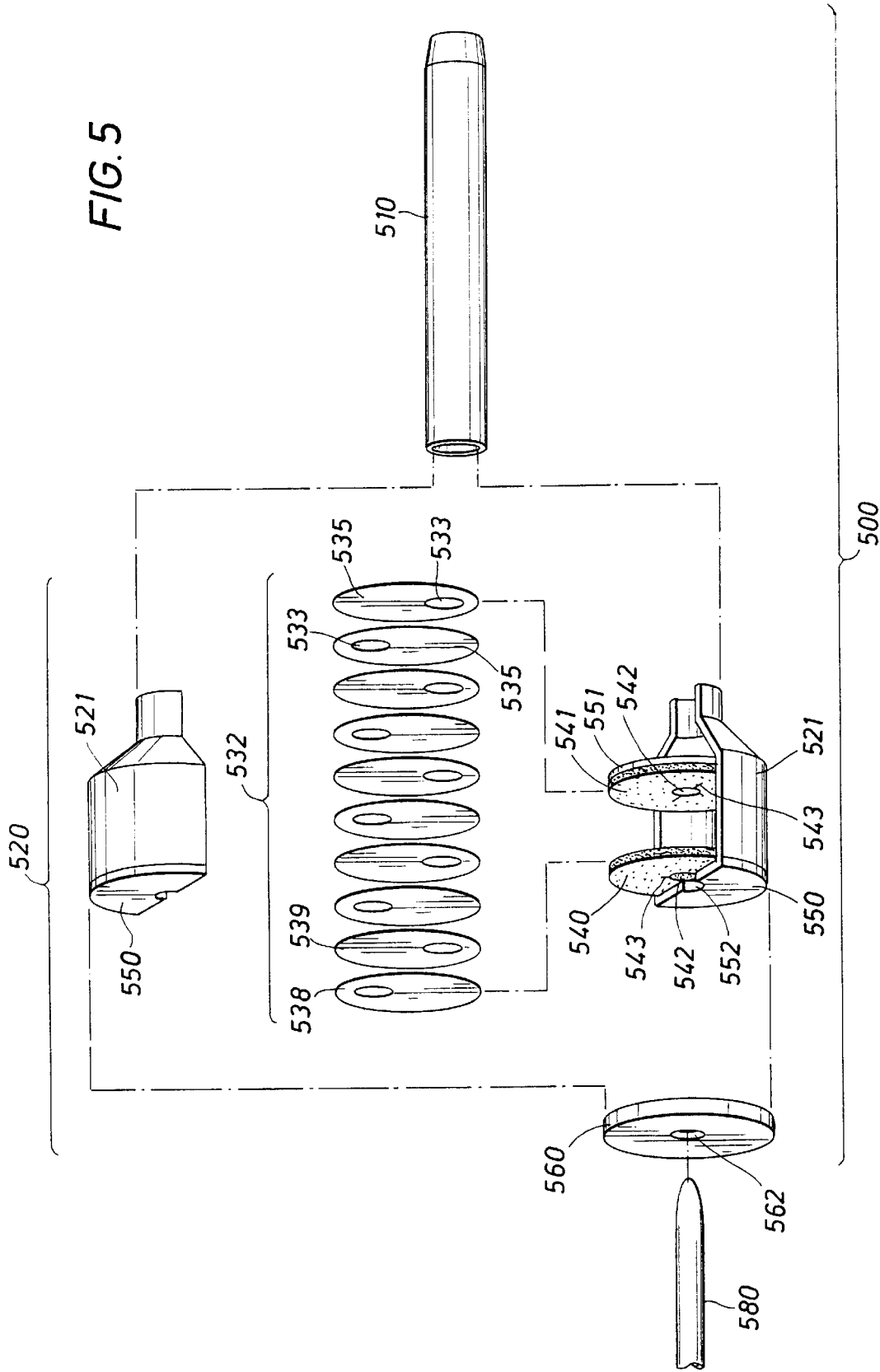

VALVE ASSEMBLY

BACKGROUND OF THE INVENTION

The present invention relates to valves. In particular, the present invention relates to valves to seal an access that can also accommodate a device there through.

BACKGROUND OF THE RELATED ART

In the last several years, minimally invasive surgical procedures have become increasingly common. Laparascopic procedures, treatment of vasculature, and other similar procedures can be done in a minimally invasive manner. For example, an Abdominal Aortic Aneurysm (AAA) may require placement of an aortic graft at the site of the aneurysm. The graft is deployed at the site of the aneurysm by a catheter.

The AAA graft procedure referred to above involves the advancement of the catheter to the site of the aneurysm. Access by the catheter to the aneurysm can be provided through an introducer sheath placed within the Superficial Femoral Artery (SFA). The introducer sheath accommodates a host of instruments during its placement and subsequent placement of the aortic graft as described further herein. The introducer sheath includes an access tube with an internal diameter large enough to accommodate the largest instrument used during the endovascular AAA procedure, with respect to outer diameter.

Generally an introducer sheath is placed within the SFA of a patient with a portion extending into the SFA from outside the body of the patient. To place the introducer sheath in this manner, a puncture is made into the SFA with a needle. The needle is replaced by a guidewire. The guidewire provides initial access to the SFA. Subsequently, a dilator of larger outer diameter than the guidewire is used. The dilator, with the introducer sheath coaxially thereabout, is threaded over the guidewire and into the SFA. The dilator is of an outer diameter such that the introducer sheath can fit snugly around the dilator. The guidewire and the dilator can be removed leaving the introducer sheath in place to provide a means of access to the SFA which leads to the vessel to be treated.

A subsequent guidewire can be inserted into the SFA through the introducer sheath. The catheter can be inserted over the guidewire and through the introducer sheath and advanced to the aneurysm site to be treated. The AAA graft can then be deployed at the site of the aneurysm.

In the procedure described above, the introducer sheath and dilator are initially inserted. The introducer sheath then accommodates no instrument at all as the dilator and initial guidewire are removed, then accommodates another guidwire, and lastly accommodates the catheter. With respect to outer diameters of all of the instruments, there is a general increase in size from no instrument, to guidewire, to dilator and catheter size, which are of the same general size. That is, the introducer sheath accommodates a diameter range of zero (i.e. no instrument) to the size of the catheter and dilator (i.e. which can be up to about 8.28 mm) and also accommodates instrument sizes in between. For example, 0.53 mm guidewires can be used. In the given scenario the introducer sheath must include an opening to provide instrument access. Furthermore, the introducer sheath must accommodate instruments that range from 0.53 mm to 8.28 mm in diameter. This is an increase of about 1,656% from the size of the guidewire to the size of the catheter and dilator.

During the procedure described above, blood in the SFA is of a pressure higher than the pressure found outside of the body. As a result the introducer sheath is susceptible to leakage. Therefore, a valve is generally placed at the proximal portion of the introducer sheath in an attempt to control hemostasis and avoid leakage. However, as noted above, the valve includes an opening to accept instruments that can be as large as, for example, 8.28 mm in diameter, and thus, the introducer sheath remains susceptible to leakage when no instrument is present through the valve. Furthermore, a typical valve is not able to accommodate a range of instrument sizes greater than about 700% from one instrument size to the next while still controlling hemostasis. This is because typical valve material will tend to tear if expanded beyond this point.

As an alternative the valve can be composed entirely of a stronger, foam-like, material, for example. However, where this is the case, the valve will provide too much friction for instruments to easily or smoothly pass through the valve. For example, deformable instruments, such as the 8.28 mm catheter referenced above, will tend to kink or buckle during passage through the valve.

Therefore, what is desired is a valve assembly to accommodate an instrument and avoid leakage when no instrument is present. A valve assembly is also desired to easily or smoothly accommodate a wide range of instrument diameters while preventing leakage.

SUMMARY OF THE INVENTION

An embodiment of the present invention provides a valve assembly with a first valve member having a first passageway. A second valve member is provided with a second passageway. A first portion of the first passageway and a second portion of the second passageway are non-overlapping. A compression member is provided adjacent the first valve member.

In another embodiment of the invention a medical access device is provided having an access portion for positioning in a body portion of a patient. A valve assembly coupled to the access portion has first and second valve members having passageways at least partially non-overlapping. A compression member is included adjacent the first valve member.

In a method of the invention a first valve member with a first passageway is provided. A second valve member with a second passageway is placed adjacent the first valve member. A compression member is coupled to a position adjacent the first valve member.

BRIEF DESCRIPTION OF THE DRAWINGS

FIG. 5 is an exploded perspective view of an alternate embodiment of a valve assembly as part of an access device.

DETAILED DESCRIPTION OF THE INVENTION

While the present invention is described with reference to certain valve assemblies and instruments to fit there through, the invention is applicable to any valve of an access device for accessing an area that is to be kept sealed from other surrounding areas. This would include situations where access is desired for laparoscopic surgery, catheterization, other forms of minimally invasive surgical procedures, and various other forms of access systems. The invention is particularly useful when the access device is to accommodate a wide range of instrument sizes or to provide access to (or from) an area of higher pressure than other surrounding areas.

Figure 1:
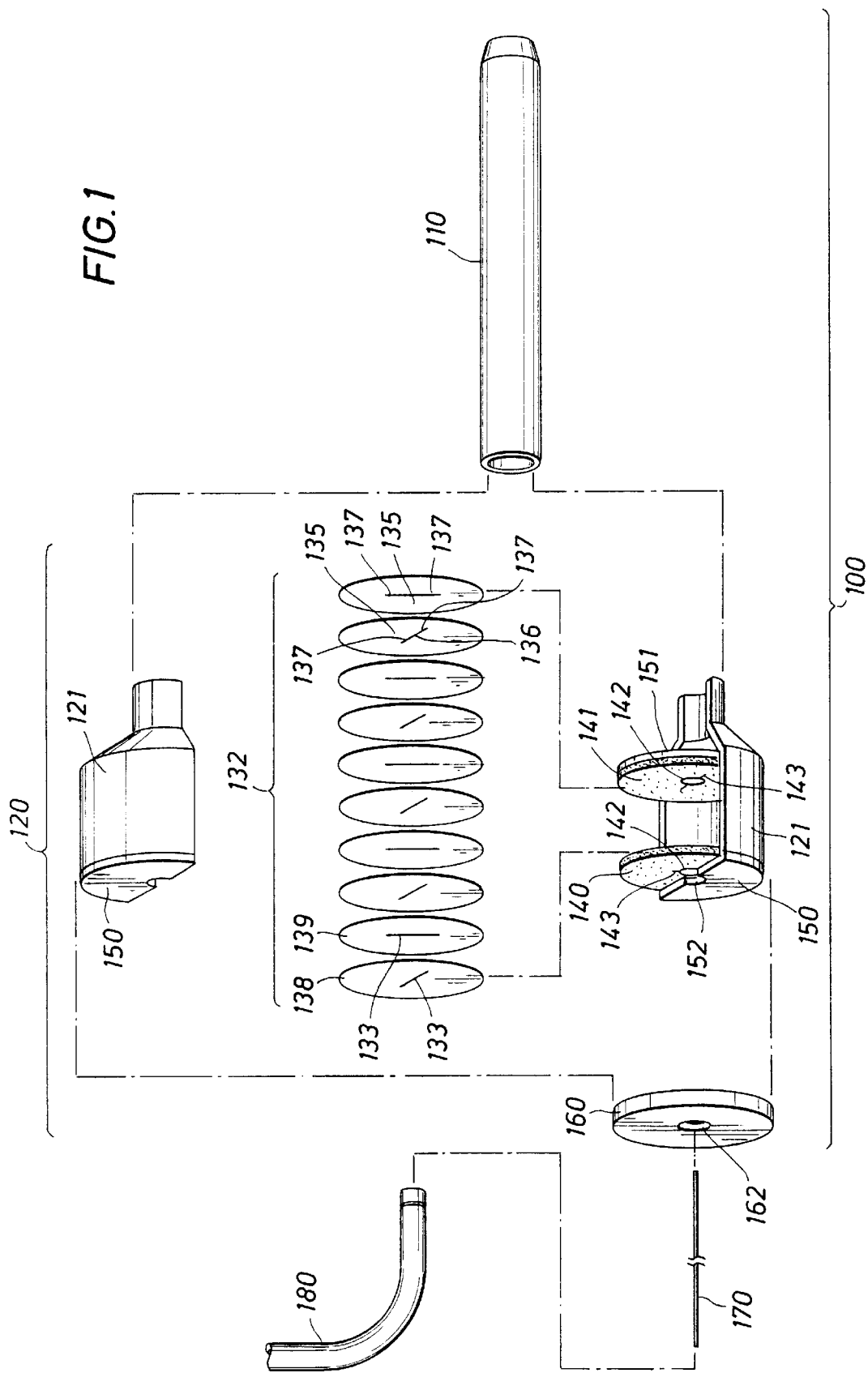
FIG. 1 is an exploded perspective view of an embodiment of a valve assembly as part of an access device.

Referring to FIG. 1, an embodiment of a valve assembly 120 is shown that is part of an access device 100. In one embodiment of the invention, the access device 100 is an introducer sheath for vascular intervention. The access device 100 provides access to a conduit such as an SFA. The access device 100 includes an access tube 110 coupled to the valve assembly 120. In other embodiments of the invention, the access device 100 is a device, other than an introducer sheath, to provide access to areas other than a conduit. For example, in one embodiment, the access device 100, including the valve assembly 120, provides access to a body cavity for performing a laparoscopic procedure.

The valve assembly 120 includes a housing 121 to contain a plurality of valve members 132. In the embodiment shown, 10 valve members 132 are used. However, in alternate embodiments of the invention, alternate numbers of valve members are used. For example, in one embodiment of the invention, 12 valve members 132 are used.

Embodiments of the invention include valve members 132 made of silicone, latex, and/or polyurethane. However, in other embodiments of the invention, other materials may be used. In the embodiment shown, where the access device 100 is an introducer sheath, the valve members 132 are between about 0.001 and about 0.004 inches thick, and preferably between about 0.00225 and about 0.00275 inches thick. In another embodiment of the invention valve members 132 are preferably thicker than about 0.002 inches thick, where the access device 100 is a laparoscopic or other type of access device 100 to accommodate non-deformable or more robust instruments.

In the embodiment shown, each of the valve members 132 contains a passageway in the form of a slit 133 or cut which allows a portion of the valve member 132 to open, for example, upon insertion of an instrument such as a guidewire 170, or other medical device tool, through the valve assembly 120. The embodiment of the slit 133 shown is linear, but other-slit shapes may be employed. In one embodiment of the invention, the slits 133 are up to about 3 mm in length and particularly adept at accommodating an instrument of up to about 8.5 mm in diameter, such as a catheter 180 or other vascular intervention device. However, slit length can vary. For example, in one embodiment of the invention, longer slits 133 are provided to accommodate larger instruments such as laparoscopic tools.

In the embodiment shown, slits 133 of adjacent valve members 132 include an overlapping portion 136 where the slits 133 of the adjacent valve members 132 overlap with one another. The slits 133 of the adjacent valve members 132 also include a non-overlapping portion 137 where the slits 133 of the adjacent valve members 132 overlap with a surface 135 of an adjacent valve member 132. In the embodiment shown, adjacent slits 133 of adjacent valve members 132 are linear and positioned substantially perpendicular to one another such that the slits 133 of the adjacent valve members 132 overlap with one another at a single intersecting point which is the overlapping portion 136 of each slit 133. However, in other embodiments of the invention, slits 133 of adjacent valve members 132 are angled with respect to one another at angles other than 90°.

Continuing with reference to FIG. 1, compression members 140, 141 are disposed adjacent the plurality of valve members 132. The compression members 140, 141 are of a less flexible and more robust configuration than the valve members 132 and provide a compressive force toward the valve members 132. In one embodiment of the invention, the compression members 140, 141 are of a material that is within the housing 121 between the plurality of valve members 132 and stationary face plates 150, 151 of the housing 121 to provide a compressive force toward the plurality of valve members 132. The face plates 150, 151 are of any generally non-deformable material for support of the compression members 140, 141.

Figure 8:
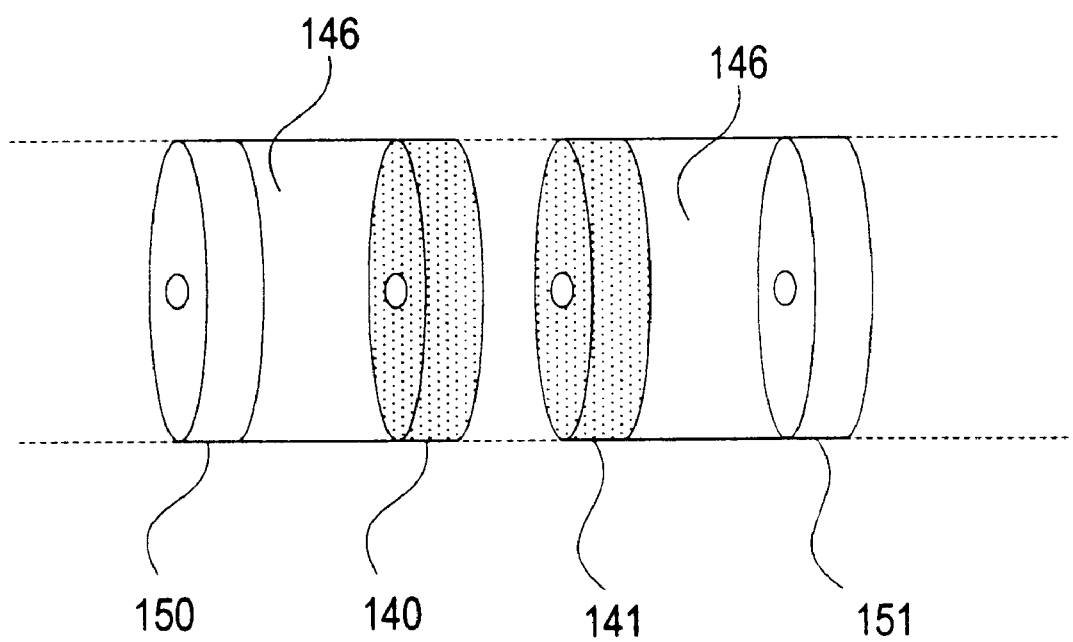
FIG. 8 is a cross-section view of a compression member that includes a spring biasing mechanism.

In one embodiment of the invention, the compression members 140, 141 are of a compressed foam. In another embodiment of the invention, the compression members 140, 141 are of a closed cell foam. One embodiment of the invention includes compression members 140, 141 of an open cell polyurethane foam compressed to about half of its natural thickness to compress the valve members 132. In another embodiment of the invention, the compression members 140, 141 are of a compressed elastomeric hemisphere. In yet another embodiment of the invention, the compression members 140, 141 include a spring biasing mechanism 146 as illustrated in FIG. 8 forcing the compression members 140, 141 away from the face plates 150, 151 to provide compression to the plurality of valve members 132. In other embodiments of the invention, other configurations of compression members 140, 141 are provided to provide compression toward the plurality of valve members 132.

Both compression members 140, 140 may not be required in all applications. For example, a single compression member 140 could be used in some situations. Similarly, in another embodiment of the invention, a single face plate 150 is used. However, in an embodiment that optimizes hemostatic or other sealable control, the valve assembly 120 includes both face plates 150, 151 and both compression members 140, 141. Additionally, in this embodiment, the compressive force exerted by at least one of the compression members 140, 141 toward the plurality of valve members 132 is maximized.

In the embodiment shown compression members 140, 141 include a passageway with an opening 142 and a compression slit 143. The compression slit 143 is perpendicular to the slit 133 of the first valve member 138 of the plurality of valve members 132 adjacent a compression member 140. In one embodiment of the invention, the opening 142 is of a cone, truncated cone or other hollowed shape to guide receipt of an instrument, such as a guidewire 170, there through. Both the opening 142 and the compression slit 143 may not be required. In one embodiment of the invention, only an opening 142 is provided for receipt of an instrument, such as a guidewire 170. In another embodiment of the invention, only a compression slit 143 is provided through which an instrument, such as a guidewire 170 may be advanced.

The face plates 150, 151 are of a generally non-deformable character or otherwise stationary. Therefore, the face plates 150, 151 include plate openings 152 to allow passage of an instrument, such as a guidewire 170, into or out of the valve assembly 120.

In the embodiment shown, the valve assembly 100 includes a cap 160 which fits over the proximal end of the housing 121. The cap 160 includes a cap opening 162 to allow passage of an instrument there through. The cap 160 may not be required. For example, in one embodiment of the invention, the face plate 150 at the proximal end of the housing 121 also acts to close off the proximal portion of the housing 121 such that no cap 160 is required.

Continuing with reference to the embodiment shown in FIG. 1, the access tube 110 of the access device 100 is configured to provide access to an SFA for delivery of an aortic graft at the site of an abdominal aneurysm. In the embodiment shown, the aortic graft is contained within a catheter 180. The catheter 180 has an outer diameter of up to about 8.5 mm.

Once the access tube 110 of the access device 100 is partially inserted into the SFA, access to the abdominal aneurysm is provided from outside the body of a patient. To advance the catheter 180 to the site of the aneurysm a guidewire 170 is first advanced through the access device 100 and the SFA to a position near the site of the abdominal aneurysm. In the embodiment shown, the guidewire 170 is no more than about 0.53 mm in diameter. However, in other embodiments other guidewire 170 diameter sizes, such as about 0.97 mm are used. Once the guidewire 170 is positioned as indicated, the catheter 180 can then be tracked over the guidewire 170 and advanced through the access device 100 and the SFA to the site of the aneurysm for delivery of an aneurysm graft.

In the embodiment discussed above, the access device 100, which is used as an introducer sheath, is first partially inserted into the SFA where it remains for a time without any instrument there through. Nevertheless, the configuration of the valve assembly 120 controls hemostasis at this time and prevents leakage of blood through the introducer sheath 100. Even in a hypertensive patient, where the mean arterial pressure exceeds about 90 mm of mercury, the configuration of the valve assembly 120 continues to control hemostasis.

In the embodiment shown, a guidewire 170 of no more than about 0.53 mm in diameter is inserted through the valve assembly 120 followed by insertion of a catheter 180 of up to about 8.5 mm in outer diameter. Nevertheless, the valve assembly 120 is able to accommodate both devices while continuing to control hemostasis. The catheter 180 does not encounter undue friction and does not buckle as it is advanced through the valve assembly 120. Additionally, the valve members 132 are not torn or damaged as the catheter 180 is advanced through the valve assembly 120. To further ensure smooth passage of instruments through the valve assembly 120, an embodiment of the invention utilizes a lubricant, such as silicone oil, between valve members 132 and at compression slits 143 or opening 142.

In the embodiment shown, the valve assembly 120 is incorporated with an access device 100 that is used as an introducer sheath. Instruments of up to about 8.5 mm in outer diameter are accommodated and a seal against more than about 90 mm of mercury is provided. However, in another embodiment of the invention, a valve assembly 120 can be used with an alternate type of access device 100. For example, in one embodiment of the invention, the valve assembly 120 is incorporated with an access device 100 to accommodate instrument sizes having outer diameters exceeding 8 mm. In one such embodiment slits 133 greater than about 2.25 mm in length are provided. In another such embodiment a compression member 140, providing a compressive force greater than that of compressed open cell foam is provided. In these manners, instrument sizes of greater than about 8 mm can smoothly be inserted through the valve assembly without causing damage to the valve members 132. In these embodiments the valve assembly 120 can continue to seal against a fluid, gas or liquid, even when exerting a pressure toward the valve assembly 120.

As noted above, embodiments of the valve assembly 120 can prevent leakage of a fluid from an area having a pressure of over 90 mm of mercury, even with no instrument inserted through the valve assembly. Additionally, the valve assembly 120 can accommodate instruments of a wide range of sizes. In spite of the wide range of instrument sizes, deformable instruments can be inserted through the valve assembly 120 without buckling. Additionally, less deformable instruments can be inserted through the valve assembly 120 without causing damage to the valve members 132. Embodiments of the invention also allow a range of instruments that differ in outer diameter size by more than 700%, to pass through the valve assembly 120 without losing hemostatic or other sealable control, damaging valve members 132, or resulting in too much friction to allow passage of the instruments through the valve assembly 120.

Figure 2:
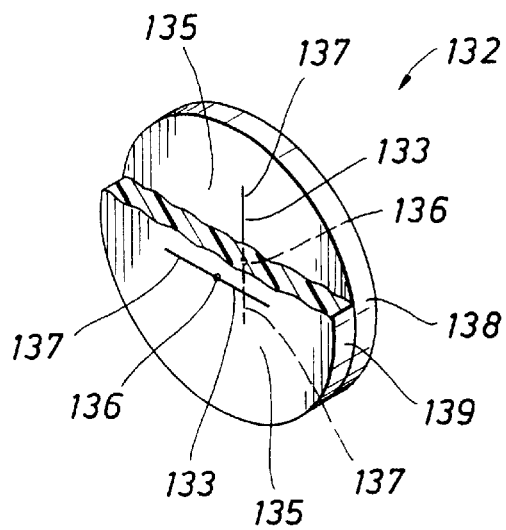
FIG. 2 is a perspective sectional view of valve members of the valve assembly of FIG. 1.

Referring to FIG. 2, adjacent valve members 138, 139 of the plurality of valve members 132 of FIG. 1 are shown. Slits 133 of the adjacent valve members 138, 139 each include the overlapping portion 166 where the slits 133 overlap with one another. As an instrument is advanced through the valve assembly 120 (see FIG. 1), it penetrates the valve members 138, 139 with a focus directed at the overlapping portion 166 of each valve member 138, 139. However, the non-overlapping portions 137, which make up the remainder of the slits 133, are adjacent a surface 135 of an adjacent valve member 138, 139 at all times. Therefore, for example, the surface 135 of a first valve member 138 supports the non-overlapping portions 137 of the adjacent second valve member 139. This support is enhanced due to the fact that compressive forces are applied to force the valve members 138, 139 toward one another.

Continuing with reference to FIG. 2, an embodiment of the invention is shown where the slits 133 of the adjacent valve members 138, 139 are perpendicular to one another. This arrangement maximizes the support that, for example, the surface 135 of the first valve member 138 is able to provide to a non-overlapping portion 137 of the second valve member 139.

Figure 3:
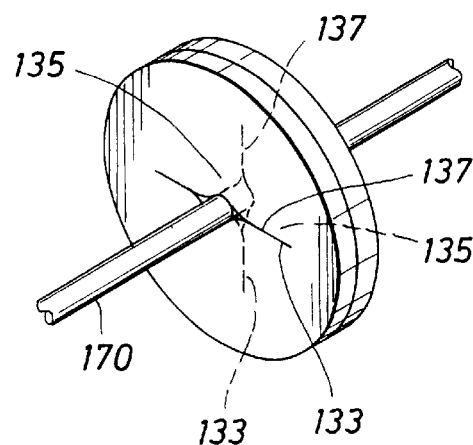
FIG. 3 is a perspective view of valve members of the valve assembly of FIG. 1.
Figure 4:
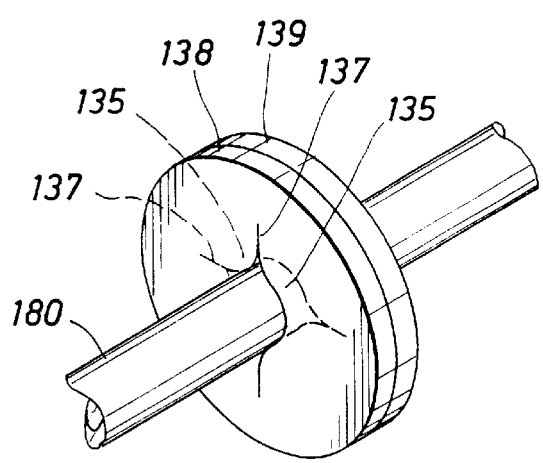
FIG. 4 is a perspective view of valve members of the valve assembly of FIG. 1.

Referring to FIGS. 3 and 4, the valve members 138, 139 of FIG. 2 are shown with a smaller instrument, such as a guidewire 170, and a larger instrument, such as a catheter 180, there through. As the instruments 170, 180 are inserted through the valve members 138, 139, the slits 133 of the valve members 138, 139 open to accommodate the instruments 170, 180. For both valve members 138, 139, a portion of the non-overlapping portions 137 also opens. However, due to the configuration of the embodiment shown, each open portion of the non-overlapping portions 137 is adjacent a surface 135 of an adjacent valve member 138, 139. In fact, the surfaces 135 of the each valve member 138, 139 are being compressed toward the open portion of the non-overlapping portions 137. Therefore, no continuous unoccupied opening or channel is present through both valve members 138, 139. As a result, hemostatic or other sealable control remains.

Referring to FIG. 5, an alternate embodiment of a valve assembly 520 is shown. In the embodiment shown, the valve assembly 520 is part of an access device 500 that is a laparoscopic access device to accommodate a laparoscopic tool 580. However, in alternate embodiments, the access device 500 can be used as an alternative device to accommodate alternative types of tools. For example, in one embodiment of the invention the access device 500 is used as an introducer sheath. An access tube 510, for at least partial insertion into an abdominal cavity of a patient, is coupled to the valve assembly 520.

A housing 521 of the valve assembly 520 is provided that houses a plurality of valve members 532. In the embodiment shown, the valve members 532 include passageways in the form of openings 533 which are entirely non-overlapping with respect to adjacent valve members 538, 539. Nevertheless, the valve members 532 are elastomeric and deformable to accommodate an instrument, such as a laparoscopic tool 580, there through. In another embodiment of the invention, the openings 533 of adjacent valve members (e.g. 538, 539) are partially overlapping. However, openings 533 of adjacent valve members (e.g. 538, 539) are radially disposed with respect to one another such that at least a portion of each of the openings 533 is non-overlapping. Additionally, in one embodiment of the invention, the plurality of valve members 532 include no residual opening portion common to all valve members 532. However, in another embodiment of the invention where an instrument, such as a laparoscopic tool 580, is to be accommodated whenever access to a body of a patient is present, the valve members 532 include a residual opening portion common to all valve members 532.

Continuing with reference to FIG. 5, compression members 540, 541 are disposed adjacent the plurality of valve members 532 to provide a compressive force toward the valve members 532. In the embodiment shown, the compression members 540, 541 include compression slits 543 and openings 542 to allow passage of an instrument. In other embodiments of the invention, only a compression slit 543 or only an opening 542 is provided for passage of an instrument.

Face plates 550, 551, of a generally non-deformable material provide support for the compression members 540, 541 to act against the valve members 532. The face plates 550, 551 include plate openings 552 to allow passage of an instrument. In the embodiment shown, a cap 560 with a cap opening 562 is included over the housing 521. However, in another embodiment of the invention, the cap 560 is not provided as the proximal-most face plate 550 closes off the housing 521.

The embodiment shown in FIG. 5 provides sealable control as the access tube is partially inserted into a body of a patient, even with no instrument present through the valve assembly. Inflation pressure, generally in the form of $CO_2$ gas, is prevented from coming through the valve assembly 520. Additionally, a larger laparoscopic instrument 580 can smoothly pass through the valve assembly 520 without causing damage to the valve members 532. In one embodiment of the invention the openings 533 are up to about 3 mm across (or in length) and the valve assembly 520 accommodates instruments up to about 8.5 mm in outer diameter size. In one embodiment, the openings 533 are circular and this length across is a diameter. In other embodiments of the invention openings 533 greater than about 2.25 mm across are used and instruments greater than about 8 mm in outer diameter are accommodated.

Figure 6:
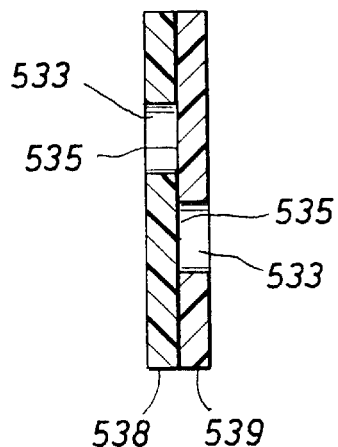
FIG. 6 is a cross-sectional view of valve members of the valve assembly of FIG. 5.
Figure 7:
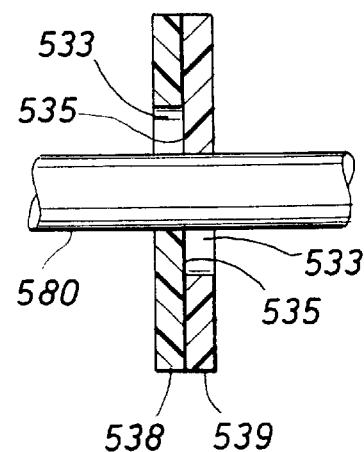
FIG. 7 is a cross-sectional view of valve members of the valve assembly of FIG. 5

Referring to FIGS. 6 and 7, adjacent valve members 538, 539 of FIG. 5 are shown. Each opening 533 of each adjacent valve member 538, 539 is adjacent a surface 535 of the adjacent valve member 538, 539. In this manner, the valve assembly 520 (see FIG. 5) provides a seal against a fluid pressure from within a body of a patient accessed by the access tube. Compressive forces directing the valve members 538, 539 toward one another ensures the integrity of the seal.

Referring to FIG. 7, the seal provided by the valve assembly 520 is shown with respect to adjacent valve members 538, 539 having an instrument, such as a laparoscopic instrument 580, there through. Even though the valve members 538, 539 have deformed and the openings 533 are forced to overlap by insertion of the laparoscopic instrument 580, all portions of the openings 533 not occupied by the laparoscopic instrument 580 continue to be adjacent a surface 535 of an adjacent valve member 538, 539. Therefore, a seal is maintained.

Embodiments of the invention include valve assemblies used with access devices to accommodate a wide range of instruments while avoiding leakage from or into an area that is to be accessed. Additionally, embodiments of the invention help avoid leakage from or into the area to be accessed when no instrument is present through the access device. Although exemplary embodiments of the invention describe particular valve assemblies, access devices and procedures, additional embodiments of the invention are possible. Many changes, modifications, and substitutions may be made without departing from the spirit and scope of this invention.

I claim:

1. A valve assembly comprising:
   a first valve member having a first passageway;
   a second valve member adjacent said first valve member, said second valve member having a second passageway, a first portion of said first passageway and a second portion of said second passageway non-overlapping;
   a compression member adjacent said first valve member to direct a force toward said first valve member, said compression member being more robust than said first valve and said second valve; and
   a housing to house said first valve member, said second valve member, and said compression member.

2. The valve assembly of claim 1 wherein said valve members are comprised of a material selected from a group consisting of silicone, latex and polyurethane.

3. The valve assembly of claim 1 further comprising a lubricant disposed between said first valve member and said second valve member.

4. The valve assembly of claim 1 further comprising a stationary face plate adjacent said compression member, said compression member between said stationary face plate and said first valve member.

5. The valve assembly of claim 1 wherein said compression member includes a spring biasing mechanism.

6. The valve assembly of claim 1 wherein said compression member is a foam selected from a group consisting of compressed foam, cell foam, and polyurethane foam.

7. The valve assembly of claim 6 wherein said compressed foam is compressed to about half of a natural thickness of said compressed foam.

8. The valve assembly of claim 1 wherein said first passageway is in the form of a first slit and said second passageway is in the form of a second slit.

9. The valve assembly of claim 8 wherein said first slit is perpendicularly adjacent said second slit.

10. The valve assembly of claim 8 wherein said first passageway includes a first overlapping portion and said second passageway includes a second overlapping portion, said first overlapping portion and said second overlapping portion overlapping.

11. The valve assembly of claim 1 wherein said compression member includes a third passageway.

12. The valve assembly of claim 11 wherein said third passageway is lubricated.

13. The valve assembly of claim 11 wherein said third passageway is of a shape to guide an instrument through said compression member.

14. The valve assembly of claim 11 wherein said third passageway is a compression slit.

15. A valve assembly comprising:
   a first valve member having a first passageway;
   a second valve member adjacent said first valve member, said second valve member having a second passageway, a first portion of said first passageway and a second portion of said second passageway non-overlapping, wherein said first passageway is in the form of a first opening and said second passageway is in the form of a second opening;
   a compression member adjacent said first valve member to direct a force toward said first valve member, said compression member being more robust than said first valve and said second valve; and
   a housing to house said first valve member, said second valve member, and said compression member.

16. A medical access device comprising:
   an access portion to be at least partially positioned within a body portion of a patient; and
   a valve assembly coupled to said access portion, said valve assembly having a first valve member with a first passageway and a second valve member with a second passageway, said first valve member adjacent said second valve member, a first portion of said first passageway and a second portion of said second passageway non-overlapping, said valve assembly including a compression member adjacent said first valve member, said compression member being more robust than said first valve and said second valve, wherein said valve assembly further includes a housing to house said first valve member and said second valve member.

17. The medical access device of claim 16 wherein said first valve member is of a thickness between about 0.001 and about 0.004 inches.

18. The medical access device of claim 16 wherein said first passageway is up to about 3 mm in length across.

19. The medical access device of claim 16 wherein said access portion and said valve assembly are configured to accommodate a medical device tool of up to about 8.5 mm in outer diameter.

20. The medical access device of claim 16 wherein said body portion is a body lumen.

21. A valve assembly comprising:
   a first valve member having a first passageway;
   a second valve member adjacent said first valve member, said second valve member having a second passageway, a first portion of said first passageway and a second portion of said second passageway non-overlapping;
   a foam member adjacent said first valve member to direct a force toward said first valve member, said foam member being less flexible and more robust than said first valve and said second valve; and
   a housing to house said first valve member, said second valve member, and said foam member.

22. A valve assembly comprising:
   a first valve member having a first passageway;
   a second valve member adjacent said first valve member, said second valve member having a second passageway, a first portion of said first passageway and a second portion of said second passageway non-overlapping, wherein said first passageway is in the form of a first opening and said second passageway is in the form of a second opening;
   a foam member adjacent said first valve member to direct a force toward said first valve member, said foam member being more robust than said first valve and said second valve; and
   a housing to house said first valve member, said second valve member, and said foam member.

23. The valve assembly of claim 22 wherein said foam member is compressed.

24. A medical access device comprising:
   an access portion to be at least partially positioned within a body portion of a patient; and
   a valve assembly coupled to said access portion, said valve assembly having a first valve member with a first passageway and a second valve member with a second passageway, said first valve member adjacent said second valve member, a first portion of said first passageway and a second portion of said second passageway non-overlapping, said valve assembly including a foam member adjacent said first valve member, said foam member being less flexible and more robust than said first valve and said second valve, wherein said valve assembly further includes a housing to house said first valve member and said second valve member.

25. The valve assembly of claim 24 wherein said foam member is compressed.

* * * * *